US00PP20001P3

(12) United States Plant Patent

Cosner et al.

(10) Patent No.: US PP20,001 P3

(45) Date of Patent: May 19, 2009

(54) *IMPATIENS* PLANT NAMED 'TISALMON'

(50) Latin Name: *Impatiens walleriana*
Varietal Denomination: TiSalmon

(76) Inventors: Harlan B. Cosner, 14389 E. Evans Creek Rd., Rogue River, OR (US) 97537; Susan Cosner, 14389 E. Evans Creek Rd., Rogue River, OR (US) 97537

( * ) Notice: Subject to any disclaimer, the term of this patent is extended or adjusted under 35 U.S.C. 154(b) by 76 days.

(21) Appl. No.: 11/728,229

(22) Filed: Mar. 23, 2007

(65) Prior Publication Data

US 2008/0235835 P1 Sep. 25, 2008

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent L Bell
(74) *Attorney, Agent, or Firm*—Ganz Law P.C.

(57) ABSTRACT

A new double *Impatiens walleriana* plant named 'TiSalmon', producing salmon flowers; dark green foliage; fully double flowers held above or beyond the foliage on strong peduncles and pedicels; and a compact mounded growth habit.

1 Drawing Sheet

Latin name of the genus and species: *Impatiens walleriana.*
Variety denomination: 'TiSalmon'.

BACKGROUND OF THE INVENTION

1. Field of Invention

The novel plant comprises a new and distinct cultivar of plant, botanically known as *Impatiens walleriana,* hereinafter referred to by the cultivar name 'TiSalmon', which is shown in the photograph accompanying this specification.

The cultivar was developed and selected in a controlled breeding program in a controlled environment in Rogue River, Oreg., by the inventors, Harlan Cosner and Sue Cosner, as described herein. The plants may be used in landscaping, window and hanging baskets and flower gardens. The plants are generally classed as an annual bedding plant.

2. Description of the Relevant Prior Art

'TiSalmon' is compared with *Impatiens walleriana* named 'Neon Salmon', subject of U.S. Plant Pat. No. 11,549. The *Impatiens* plant differs from prior plants, namely 'Neon Salmon' in at least the following ways:

1. 'Neon Salmon' does not flower as well in the heat as 'TiSalmon.'
2. See accompanying comparison chart.

These and other distinguishing characteristics will be apparent to persons skilled in the art.

DISCOVERY AND PARENTAGE

The cultivar was developed by standard cross-pollination. The pollen producing parent was an unpatented pollen producing double-flowered *Impatiens walleriana,* and the seed producing parent was an unpatented semi-double-flowered *Impatiens walleriana.* The seed parent's flower color was light orange, and the pollen parent's flower was salmon. Neither parent is either patented or commercially available.

The cross was made in the breeders' controlled breeding program at Rogue River, Oreg. The first asexual reproduction was made at Rogue River, Oreg., and was produced from cuttings in the breeder's greenhouse. The cuttings were lateral stems with two or more leaves. Successive asexual generations produced from cuttings with two or more leaves have shown the cultivar to be stable and reproduced true to type. 'TiSalmon' is both male and female sterile.

SUMMARY

The cultivar is unique either in one or in combination of the characteristics described herein. It is a new double-flowered *Impatiens walleriana* producing salmon colored flowers; dark green foliage; fully double flowers held above or beyond the foliage; and a mounded growth habit.

BRIEF DESCRIPTION OF THE DRAWING

This new *Impatiens* plant is illustrated by the accompanying photographic drawing which shows blooms, buds, and foliage of the plant in full color, the color showing being as true as can be reasonably obtained by conventional photographic procedures. There may be variations between the colors in the photograph and the colors in the following description due to light reflectance, or the amount of blue or red light captured in the film. If such variations occur, the written description shall control.

DETAILED DESCRIPTION

The following description was taken on Sep. 17, 2006. The photograph illustrates the overall appearance of the cultivar described herein. The accompanying color photograph was taken of a 'TiSalmon' plant of about 10 weeks of age from rooted cuttings at first inflorescence and illustrates a plant of 'TiSalmon' grown in summer and just beginning to mature.

Color references are according to The Royal Horticultural Society Chart, except where general terms of ordinary dictionary significance are used.

The following description was taken from a plant of 'TiSalmon' grown under the following environment and cultural practices at Rogue River, Oreg. Phenotypical variations may result in plants grown under conditions and locations other than those listed herein.

*Container.*—6-inch Azalea pot.
*Medium.*—Peat-lite type of soilless medium.
*Greenhouse covering.*—Double layer Polyethelene with 50% shade applied above the covering.
*Minimum outdoor temperature.*—65° F.
*Maximum outdoor temperature.*—115° F.
*Light levels.*—2500–3000 ft candles.
*Fertilizer.*—20-10-20 with trace elements applied twice followed by one leaching with clear water.
*Cutting type.*—Lateral stems with two or more leaves.

Propagation:
*Type of cutting.*—Lateral stems with two or more leaves.
*Time to initiate roots.*—Generally about 7 to 10 days at soil temperature of 72° F.

Appearance and form of mature plant:
*Growth habit.*—Mounded and of compact-medium vigor.
*Plant size.*—Plants mature at about 15 cm in height and about 20 cm in width. Both of these measurements are a function of age, environmental and cultural practices, and can vary accordingly.
*Rooting habit.*—The roots are fibrous and well-branched.
*Rooting ability.*—Easy, no hormones needed.
*Stems.*—Stems are freely produced and no pinching to induce branching is needed. Color is 146C with stippling of very small markings that are difficult to determine but which appear to be close to 183C, stippling is heavier at the nodes. The stems at maturity are generally about 4 mm in diameter at the internodes, and the longest internode length is generally at least 3.5 cm in length. The stem length at maturity is generally about 10 cm.
*Foliage.*—Shape is ovate with cuneate to attenuate base; crenate margin, margin having tiny spines of an undeterminable reddish to brownish red color and each being less than 1 mm in length and protruding outwards in a perpendicular direction from leaf edge and parallel to the flat surfaces of the leaf between the lobes of the crenate margin; and an acuminate apex. Size of largest leaves is about 5 cm long; about 3.5 cm wide.
*Foliage color.*—Adaxial surface close to 147A; abaxial surface close to 147C; abaxial surface venation is close to 148A; adaxial surface venation is barely distinguishable, main vein at base is closest to 146A, lateral veins are close to 146A.
*Foliage texture.*—Smooth and flat.
*Petioles.*—Longest petioles are about 2.5 cm long, half round, flat to slightly convex on upper surface which is about 3 mm wide, thickness (from the upper surface to the bottom surface) of about 1.5 mm. Adaxial surface color appears to be 147C; abaxial surface color appears to be close to 146C to 146D.
*Flower habit.*—Flowers are produced continuously throughout the flowering season.
*Natural flowering season.*—Year around in greenhouse conditions, and the frost free period from spring through fall when planted outdoors.
*Duration of flower.*—Each flower generally lasts about 4 days at 110° F. maximum and 65° F. minimum temperature.
*Flowers borne.*—Above or beyond the foliage.
*Flower texture.*—Smooth and satiny.
*Flower color.*—Largest Petals/petaloids — Adaxial surface is closest to 52A, but is slightly more orange tinged, with a purplish basal spot close to 66A. Abaxial surface is closest to 52D.
*Quantity.*—Usually two or more open flowers per stem.
*Petal/petaloid count.*—Generally 25 or more.
*Size.*—Flowers are generally about 5 cm in diameter; generally about 2.5 cm deep. The largest petals/petaloids are generally about 2.5 cm wide and about 2.25 cm long; obovate to exaggerated obovate in shape with obtuse to retuse apex, entire margin, and cuneate to obtuse base.
*Flower buds.*—The buds prior to opening are about 1 cm in length; about 1 cm in diameter, shape is ovate. Bud color prior to opening is close to 145A on top with a narrow ridge close to 144A in the very center; and close to 144D on bottom.
*Peduncles.*—Generally about 3 cm long; about 2 mm in diameter; color close to 148B. Good strength.
*Pedicels.*—Generally two or more per peduncle. Each is generally about 2.5 cm in length, and about 1.5 mm in diameter. Color is close to 148B. Good strength.
*Calyx.*—Calyx consists of generally one sepal and one spur. It is generally about 2.5 cm long, and about 2 mm in diameter at sepal end; shape is an acicular tapering tube about 1 mm in diameter at the apex, and it is attached toward the base of the sepal in a peltate manner. Color is close to 172C at apex, and is closest to 172A at base. The sepal generally splits down the middle as the flower opens, each half generally measures about 0.5 cm wide, and about 1 cm long; ovate in shape with an acute apex, entire margin, and obtuse to cordate base; adaxial surface is close to 145B in the center or center edges if split, lightening to 145D at the outer edges, with a basal spot where the spur is attached close to 67A where the spur connects; the abaxial surface is close to 145B and may have a stippled spot close to 145B and a hard to determine color that appears close to 61A where the spur attaches.
*Reproductive organs.*—The reproductive organs are replaced with sterile petaloids.
*Disease resistance.*—Disease resistance has not been tested.
*Dampness resistance.*—The plant has shown a good ability to hold the flowers in an outward manner during summer rains.
*Heat tolerance.*—The plant has shown a good tolerance to temperatures exceeding 100° F., at Rogue River by flowering continuously during temperatures as high as 113° F.

COMPARISON CHART TO PRIOR ART

| | 'TiSalmon' | 'Neon Salmon' |
|---|---|---|
| Stems - color | 146C markings close to 183C | Close to 146B with markings of 187B |
| Foliage - Size | about 5 cm long: about 3.5 cm wide | About 5.5 cm long; about 4 cm wide |

COMPARISON CHART TO PRIOR ART-continued

| | 'TiSalmon' | 'Neon Salmon' |
|---|---|---|
| Abaxial color | close to 147C | 147B with reddish blotches close to 183D |
| Foliage - Abaxial venation color | close to 148A | Close to 148A |
| Foliage - Adaxial color | 147A | 147A |
| Foliage - Adaxial venation color | closest to 146A | 146A, midrib 146A with very tiny spots close to 187A to 187B |
| Petiole - Size | 2.5 cm long, upper surface which is about 3 mm wide, depth of about 1.5 mm | about 2 cm long and about 3 mm width, depth about 2 mm |
| Adaxial color | 147C | 146B at leaf base, reddish tinge close to 187B at node end |
| Petiole Abaxial color | 146C to 146D | 146B |
| Petal/Petaloid - Size | generally at least 2.5 cm wide and at least 2.25 cm | about 2.1 cm in length, about 2.5 cm in width |
| Abaxial color | long closest to 52D | 52C |
| Petal/Petaloid Adaxial color | close to 52A with purplish basal spot 66A | 52A at edges, 40A from edges toward base with a basal spot of 61B |
| Peduncle - Size | generally at least 3 cm long, about 2 mm in diameter | about 2 cm long, about 2 mm in diameter |
| Color | close to 148B | 146C to 146D |
| Pedicel- Size | 2.5 cm in length, and at least 1.5 mm in diameter | about 2 cm in length, 1.5 mm in diameter |
| Color | color is close to 148B | 146C to 146D |
| Sepal -Size | generally splits with each half being about 0.5 cm wide, and 1 cm long | about 1 cm wide and about 1 cm long |
| Adaxial color | close to 145 B at center with edges to 145D | close to, but darker than 145A to 145B |
| Sepal Abaxial color | close to 145B a spot stippled with 145B and 61A | close to 145A to 145B |

COMPARISON CHART TO PRIOR ART-continued

| | 'TiSalmon' | 'Neon Salmon' |
|---|---|---|
| Spur - Size | generally at least 2.5 cm long and about 2 mm in diameter at sepal end | about 3.5 cm |
| Color | close to 172C at apex, and 172A at base | 148A |
| Buds - Size | about 1 cm in length; about 1 cm in diameter | about 0.8 cm long, about 0.6 cm diameter |
| Color | 145A on top with a narrow ridge in center close to 144A and 144D on bottom | top 145A to 145B |

COLOR CODE CHART

Color references according to the Royal Horticultural Society Chart

| | |
|---|---|
| Stems: | 146C, 183C |
| Foliage Abaxial surface: | 147C |
| Foliage Abaxial surface venation: | 148A |
| Foliage Adaxial surface: | 147A |
| Foliage Adaxial surface venation: | 146A |
| Petiole Adaxial surface: | 147C |
| Petiole Abaxial surface: | 146C, 146D |
| Petals/Petaloids Abaxial surface: | 52D |
| Petals/Petaloids Adaxial surface: | 52A, 66A |
| Buds: | 145A, 144A, 144D |
| Peduncles: | 148B |
| Pedicels: | 148B |
| Sepals adaxial surface: | 145B, 145D |
| Sepals abaxial surface: | 145B, 145B, 61A |
| Spur: | 172C, 172A |

What is claimed:

1. A new and distinct cultivar of double-flowered *Impatiens walleriana* plant named 'TISALMON,' as illustrated and described herein.

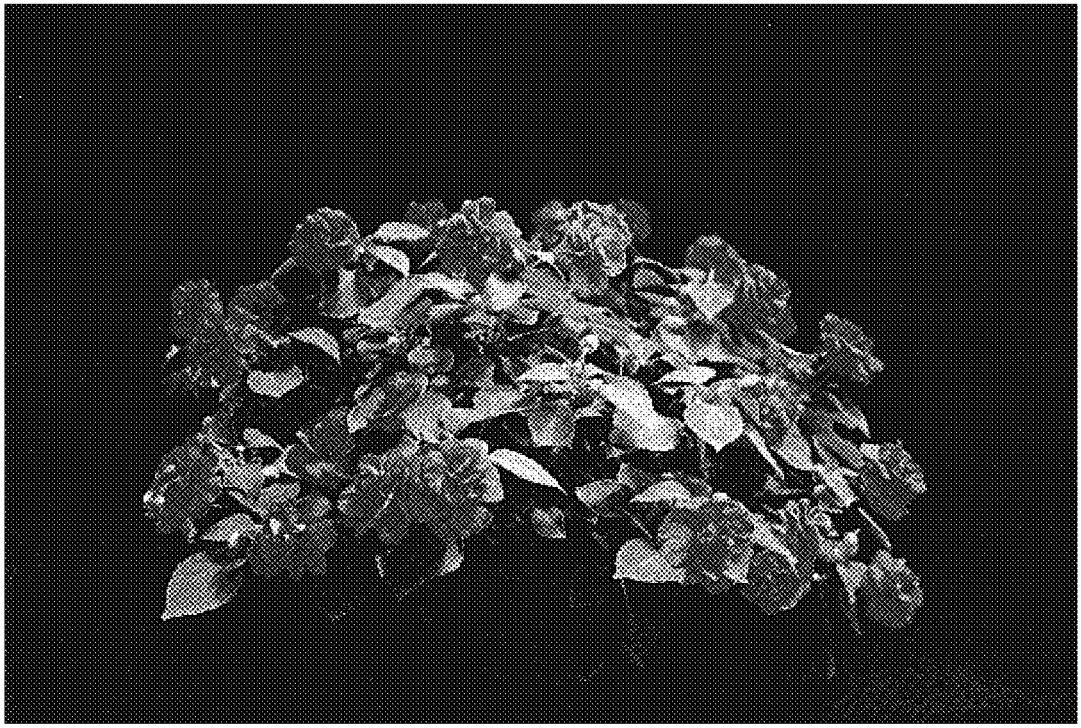

* * * * *